United States Patent [19]
Salyer

[11] Patent Number: 5,817,096
[45] Date of Patent: Oct. 6, 1998

[54] TOOL DRIVER

[75] Inventor: Paul E. Salyer, Warsaw, Ind.

[73] Assignee: Othy, Inc., Warsaw, Ind.

[21] Appl. No.: 754,939

[22] Filed: Nov. 25, 1996

[51] Int. Cl.⁶ .................................................. A61B 17/56
[52] U.S. Cl. ............................................................. 606/81
[58] Field of Search .......................... 606/89, 80, 85, 606/84, 91, 100, 99, 81; 408/124, 125

[56] References Cited

U.S. PATENT DOCUMENTS

| | | |
|---|---|---|
| 1,130,716 | 3/1915 | Dressel . |
| 3,947,047 | 3/1976 | Hultman . |
| 4,131,116 | 12/1978 | Hedrick . |
| 4,341,206 | 7/1982 | Perrett et al. . |
| 4,611,587 | 9/1986 | Powlan . |
| 4,692,073 | 9/1987 | Martindell . |
| 4,900,202 | 2/1990 | Wienhold . |
| 4,987,904 | 1/1991 | Wilson . |
| 5,013,194 | 5/1991 | Wienhold . |
| 5,116,339 | 5/1992 | Glock ........................................ 606/91 |
| 5,169,399 | 12/1992 | Ryland et al. ............................ 606/91 |
| 5,171,312 | 12/1992 | Salyer . |
| 5,171,313 | 12/1992 | Salyer ....................................... 606/86 |
| 5,180,384 | 1/1993 | Mikhail . |
| 5,236,433 | 8/1993 | Salyer . |
| 5,282,804 | 2/1994 | Salyer . |
| 5,417,696 | 5/1995 | Kashuba et al. ......................... 606/91 |
| 5,501,686 | 3/1996 | Salyer . |
| 5,540,697 | 7/1996 | Rehmann et al. ....................... 606/91 |
| 5,571,111 | 11/1996 | Aboczky .................................. 606/91 |

FOREIGN PATENT DOCUMENTS 2236019  2/1973  Germany .

*Primary Examiner*—Guy V. Tucker
*Attorney, Agent, or Firm*—Lundy and Associates

[57] ABSTRACT

A tool driver comprising a shaft having a longitudinal axis and opposite ends. A tool base is secured to the shaft at one of the ends. A plurality of tool engaging arms extend generally radially outwardly of the tool base and the shaft. The arms are moveable radially outwardly of the shaft between a tool engaging position and a retracted position. An arm actuator is positioned on the shaft to retract and extend the arms. The other end of the shaft is shaped so as to be engageable with the chuck or collet of a tool driver.

23 Claims, 2 Drawing Sheets

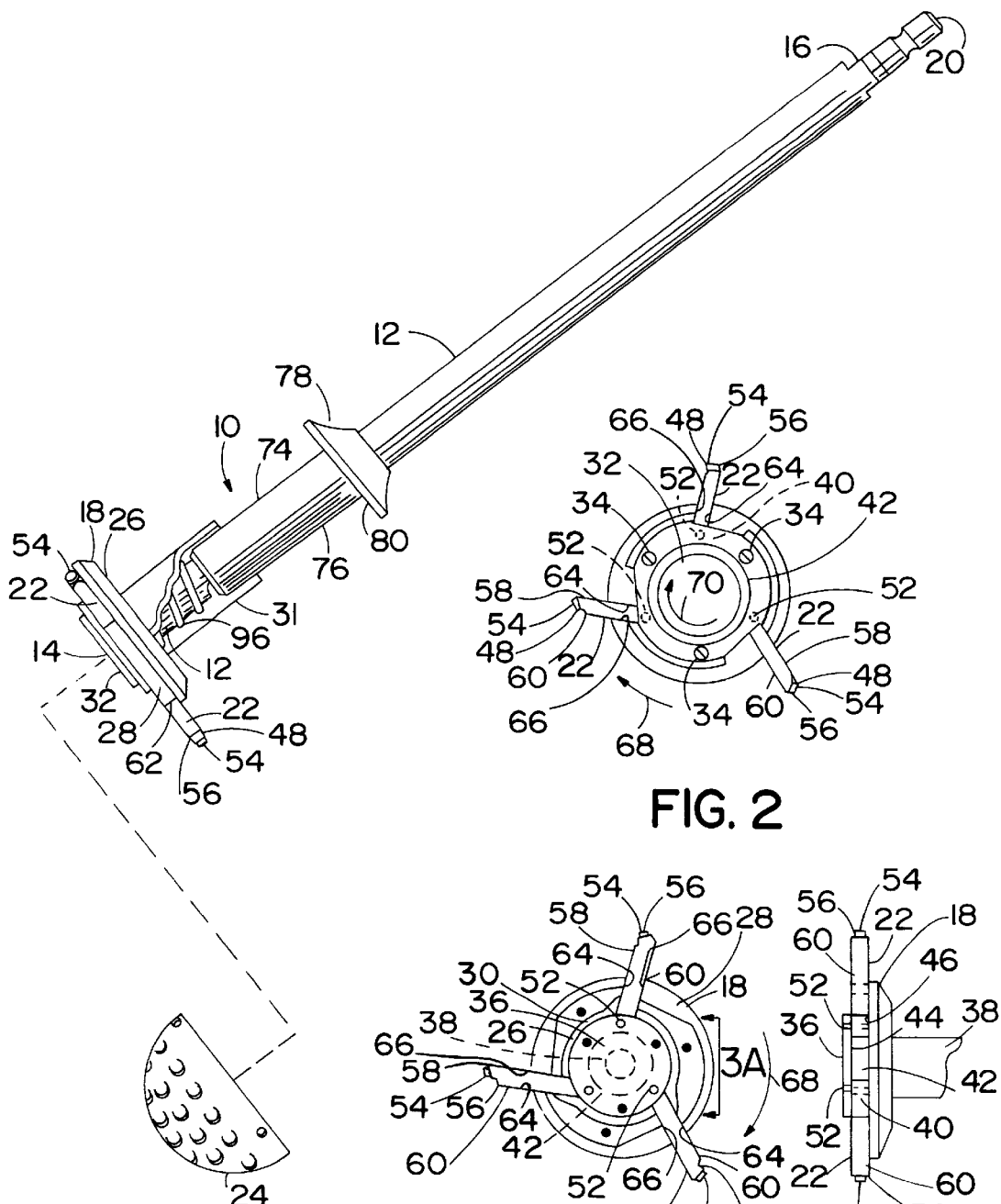

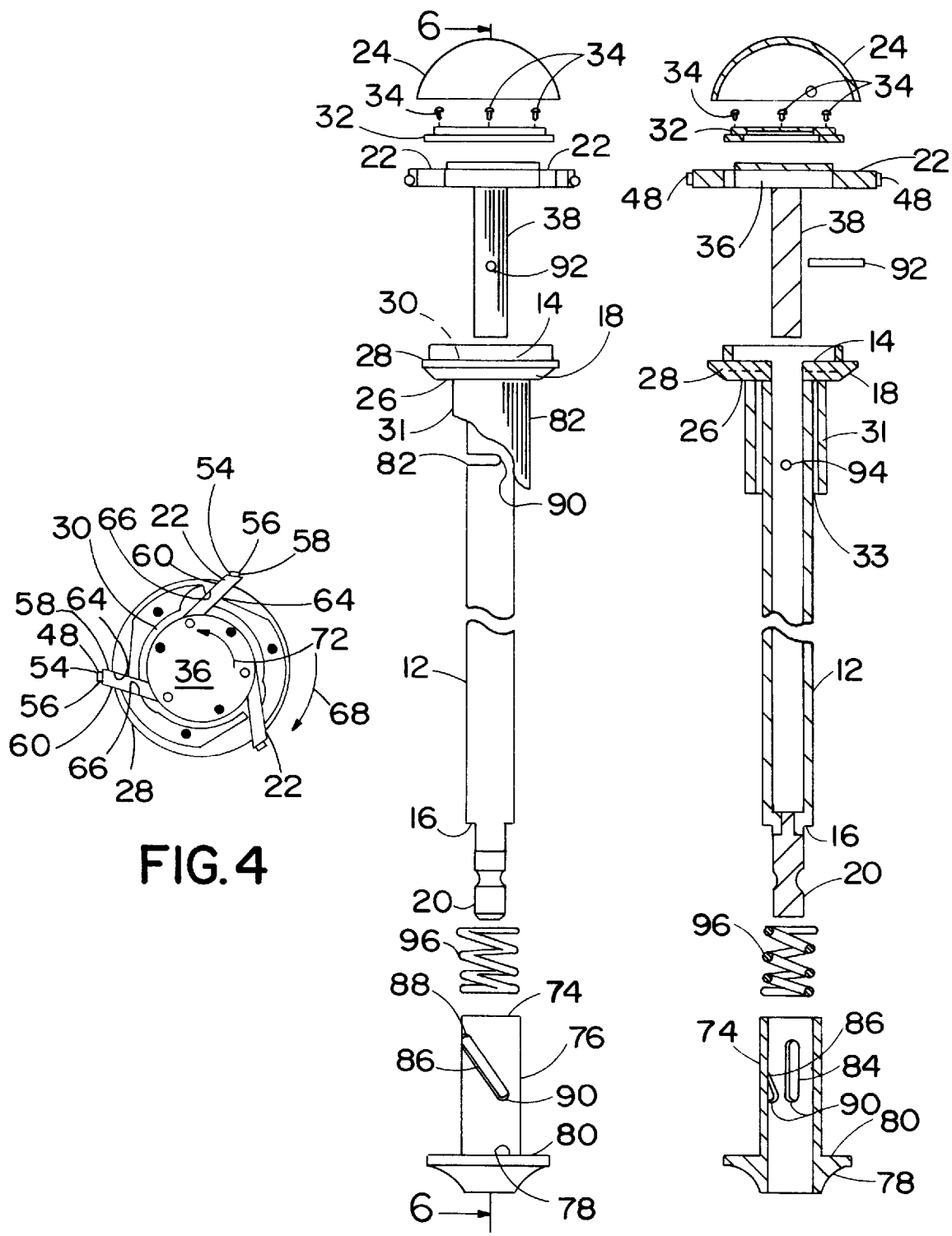

TOOL DRIVER

BACKGROUND OF THE INVENTION

The present invention relates to holders for rotary tools, and more particularly pertains to a tool driver suitable for use with open backed acetabular reamer cups, patella cutters and other surgical tools which are secured to tool drivers by diametrically opposed pins.

Acetabular reamer cups are surgical tools which are used to cut hemispherical cavities in pelvis bones for insertion of artificial hip joints. Patella cutters are surgical tools which are used to cut or shape the underside of the patella or knee cap during knee replacement surgery. Acetabular reamer cups and patella cutters are generally mounted on a tool driver, which in turn is mounted in the chuck or collet of a portable drill or flexible powered shaft for use. Patella cutters have a complex arrangement of precisely shaped cutting edges extended outwardly from a planar surface. Acetabular reamer cups have a similar arrangement of precisely shaped cutting edges extending outwardly from a spherical surface. Both acetabular reamer cups and patella cutters are spun with the tool driver when used, and need to be separable from the tool drivers to replace or sharpen as used. It may be necessary to change cutters during an operation. Tool cutters are not inexpensive and must be cleaned and reused. Therefore it is highly desirable to provide a new and improved tool driver. It is also highly desirable to provide an improved tool driver which may be cleaned and reused.

Some previous tool drivers are mounted on an end boss of a tool driver or are gripped by opposed pins or an opposed spring loaded ball catch like that on a socket wrench. See U.S. Pat. No. 5,171,313, U.S. Pat. No. 5,501,686 and U.S. Pat. No. 5,282,804. Others have a mechanism which provides for axial and rotary movement of a clamp. See U.S. Pat. No. 4,811,632, U.S. Pat. No. 5,236,433 and U.S. Pat. No. 5,171,312. Some of these drivers require two hands to lock and unlock the tool holding system. Others tend to trap dry blood and other debris which is difficult to remove during cleaning. Still others require close tolerances between the tools and the tool drivers, at greatly increased cost, to prevent free play between the cup and the tool driver such that close tolerances can be maintained in the cutting operation. Therefore it is highly desirable to provide an improved tool driver having a mechanism which does not tend to trap dried blood or other debris and can be easily cleaned and sterilized. It is also highly desirable to provide an improved tool driver which can maintain very close tolerances during the cutting operation. It is also highly desirable to provide an improved tool driver which is fully operated, single handily.

Also, many prefer the open backed surgical tools because of their lower cost and ease of debris removal during use. It is therefore highly desirable to provide an improved tool holder for such open backed surgical tools.

Additionally, the surgical tools driven by tool holders come in all sizes. In the past, a separate tool driver was provided for each size of tool. Surgical tools generally may range between 36 mm and 80 mm sizes. It is therefore highly desirable to provide an improved tool driver which can be used for driving a plurality of sizes of surgical tools.

Finally, it is highly desirable to provide an improved tool driver which has all of the above features.

SUMMARY OF THE INVENTION

It is therefore an object of the invention to provide a new and improved tool driver.

It is also an object of the invention to provide an improved tool driver which may be cleaned and reused.

It is also an object of the invention to provide an improved tool driver having a mechanism which does not tend to trap dried blood or other debris and can be easily cleaned and sterilized.

It is also an object of the invention to provide an improved tool driver which can maintain very close tolerances during the cutting operation.

It is also an object of the invention to provide an improved tool driver which is fully operated, single handily.

It is also an object of the invention to provide an improved tool holder for such open backed surgical tools.

It is also an object of the invention to provide an improved tool driver which can be used for driving a plurality of sizes of surgical tools.

It is finally an object of the invention to provide an improved tool driver which has all of the above features.

In the broader aspects of the invention, there is provided a tool driver comprising a shaft having a longitudinal axis and opposite ends. A tool base is secured to the shaft at one of the ends. A plurality of tool engaging arms extend generally radially outwardly of the tool base and the shaft. The arms are moveable radially outwardly of the shaft between a tool engaging position and a retracted position. An arm actuator is positioned on the shaft to retract and extend the arms. The other end of the shaft is shaped so as to be engageable with the chuck or collet of a tool driver.

BRIEF DESCRIPTION OF THE DRAWINGS

The above-mentioned and other features and objects of the invention and the manner of attaining them will become more apparent and the invention itself will be better understood by reference to the following description of an embodiment of the invention taken in conjunction with the accompanying drawings wherein:

FIG. 1 is a perspective view, partially broken away, showing the improved tool driver of the invention with an acetabular reamer cup exploded therefrom;

FIG. 2 is a top planar view of the improved tool driver of the invention;

FIG. 3 is a view like FIG. 2 with the top plate removed showing the driver mechanism with the arms fully extended;

FIG. 3a is a fragmentary sectional view with the cavity side walls removed for easy viewing taken substantially along the section line 3a—3a of FIG. 3.

FIG. 4 is a view like FIG. 3 showing the mechanism with its arms retracted;

FIG. 5 is a fragmentary exploded view showing all of the parts of the improved tool driver of the invention; and FIG. 6 is a sectional view like FIG. 5 taken substantially along section line 6—6 of FIG. 5.

DESCRIPTION OF A SPECIFIC EMBODIMENT

The improved tool holder 10 of the invention has a cannulated shaft 12 with opposite ends 14, 16. At end 14, a tool base 18 is secured to the shaft. At end 16 a collet 20 is secured to shaft 12. The tool base 18 has a plurality of arms 22 extending therefrom by which tools 24 can be attached to the shaft 12.

The tool base 18 has a bottom plate 26 upstanding side walls 28 defining a cavity 30. A top plate 32 is secured by a plurality of screws 34 to totally enclose cavity 30, together with side walls 28 and bottom plate 26. In the specific embodiment illustrated in the Figures, tool base 18 disc shaped, bottom plate 26 and top plate 32 are both generally disc shaped, side wall 28 is annular in shape. A sleeve 31 is secured to tool base 18 and surrounds shaft 12. Sleeve 31 defines annular space 33 therebetween with shaft 12. Shaft 12 and tool base 18 are of stainless steel, and tool base 18 and sleeve 31 are secured to shaft 12 as by welding.

An arm driver 36 is positioned within cavity 30 and secured to a rod 38. Rod 38 is telescopically positioned within the interior of cannulated shaft 12. In a specific embodiment, rod 38 is a solid stainless steel rod and arm driver 36 is a stainless steel disc with a peripheral groove 40 machined therein. Groove 40 has a bottom 42 and opposite walls 44 and 46. In a specific embodiment, the bottom 42 is a cylindrical surface and walls 44 and 46 are annular in shape.

Positioned within groove 40 are a plurality of arms 22. Each arm 22 has opposite ends 48 and 50. Ends 50 are pivotally connected between walls 44, 46 of groove 40 by pins 52. Ends 48 are distal ends which have a knob 54 and a surrounding outwardly facing surface 56. Each arm 22 is rectangular in cross-section having opposing guiding surfaces 58, 60.

Cavity wall 28 has an opening 62 therein for each of the arms 22. Each opening 62 has opposing bearing surfaces 64, 66 which engage arm surfaces 56 and 58 to guide arms during arm movement through opening 62. Arms 22 extend from arm driver 36 generally tangentially thereof through opening 62 such that when driver 36 is rotated in the direction of arrow 70 arms 22 are extended from arm driver 36 and tool base 18 so as to engage tool 24. Arms 22 extend generally tangentially of the arm driver 36 in the direction of rotation as indicated in FIG. 2. Each of the arms 22 move through the opening 62 and are guided by guiding surfaces 58, 60 and surfaces 64, 66 so as to move knob 54 generally radially of arm driver 36 and tool base 18 and shaft 12 throughout the movement of the arms 22. As the arms 22 move, the surfaces 56 which surround the knob 54 are held generally perpendicular to the radii of arm driver 36 and the tool base 18. In a specific embodiment, these surfaces may be part spherical.

Referring to FIGS. 3 and 4, FIG. 3 illustrates the arms 22 in their fully extended position after arm driver 36 has been rotated relative to the shaft 12 in the direction indicated by arrow 70. This is the same direction as the direction of rotation of the tool driver 10 as indicated by arrow 68. FIG. 4 illustrates the arms 22 in their retracted position. Arms 22 are in their fully retracted position after arm driver 36 is rotated relative to the shaft 12 in the direction of the arrow 72 indicated in FIG. 4. This direction is opposite that of the direction of rotation as indicated by arrow 68. Arm driver 36 is enclosed in cavity 30 by top plate 32. Top plate 32 is secured to the upwardly facing surface of walls 28 by screws 34.

Referring to FIGS. 5 and 6, the assemblage of the shaft 12 and the rod 38 and their attached tool base 18 and arm driver 36 will now be described. Actuator 74 is provided to have a cylindrical and tubular portion 76 and an enlarged thumb engaging end 78. Thumb engaging end has a size larger than the tubular portion 76 to so as to define an annular step 80 facing tubular portion 76. Actuator 74 is positioned on shaft 12 and is slideable axially along the shaft 12.

Actuator 74, shaft 12 and rod 38 are connected together by a series of pins and slots. Shaft 12 has a slot 82 extending transversely thereof as shown in FIG. 5. Actuator 74 has a pair of slots. Slot 84 extends axially of actuator 74 as shown in FIG. 6. Slot 86 extends angularly of the axis of tool holder 10 as shown in FIG. 5. Each of the slots 82, 84 and 86 has opposite slot ends 88, 90 which have a correspondence with the fully retracted position of the arms 22 and the fully extended position of the arms 22 as will be explained hereinafter.

Shaft 12 and rod 38 and actuator 74 are each connected together by a pair of pins 92 and 94 positioned in slots 82–86. Pin 92 is secured to rod 38 and is positioned in slots 82 and 86. Pin 94 is secured to shaft 12 and is positioned in slot 84.

A spring 96 is positioned between actuator 74 and tool base 18. Spring 96 urges tool base 18 and actuator 74 apart and biases pins 92 and 94 toward ends 88 of slots 82, 84 and 86. Thus, actuator 74 has an at rest position with pins at end 88 of slots 82, 84 and 86. This at rest position corresponds to the arms 22 fully extended as shown in FIG. 3. Once the pins 92 and 94 are secured to rod 38 and shaft 12, respectively, and positioned in slots 82, 84 and 86, the actuator is on shaft 12 and cannot be removed, the rod 38 is within shaft 12 and cannot be removed therefrom, and the improved tool driver 10 of the invention is fully assembled and operational.

In operation the improved tool driver 10 of the invention can be attached to tools of various sizes and used to drive those tools in a variety of applications. One example is in hip replacement surgery, the tools 24 may be acetabular reamer cups of the open end variety and the improved tool driver 10 can be attached to cups having a diameter from about 36 mm to about 80 mm. These cups are held secure by the arms 22 as the tool driver 10 is rotated by the drill or powered shaft. The cutting force, in this manner holds the acetabular reamer cup against the surfaces 56 and locks the cup onto the driver. Arms 22 bear the cutting force generally compressively axially along the arms 22.

In prior practice, separate tool drivers were necessary to accommodate different sizes of acetabular reamer cups ranging from 36 mm to 80 mm. Thus, the improved tool driver 10 of the invention allows one too driver 10 to be used in place of multiple prior art drivers. The open backed tools such as acetabular reamer cups 24 illustrated allows for the ease of debris removal during the use of the cup. Such debris is not as readily removed in the acetabular reamer cup of the design disclosed in U.S. Pat. No. 5,236,433.

The tool holder of the invention 10 functions similarly to that tool driver disclosed in U.S. Pat. No. 5,236,433 as that patent has an actuator functioning similarly to actuator 74. By grasping the shaft 12 with the fingers and moving actuator 74 with the thumb positioned on thumb surface 78, pins 92 and 94 can be unseated from slot ends 88 and moved toward slot end 90. As the actuator 74 is moved toward tool base 18, arm driver 36 is rotated in the direction of arrow 72 and arms 22 are retracted. When the pins 92, 94 are adjacent ends 90 of slots 82, 84 and 86, arms 22 are fully retracted and tool 24 whatever size may be disconnected from the tool driver 10 and a new tool 24 may be attached. By releasing the thumb pressure on actuator 74, pins 92, 94 will move to their at rest position at end 88 of slots 82, 84 and 86 in response to the urging of spring 96. In this manner tools 24 of a variety of size may be attached, removed and reattached to the tool driver 10. The extension and the retraction of the arms 22 is easily accomplished single handily.

The tool driver of the invention provides a new and improved tool driver which may be cleaned, reused and which does not tend to trap dried blood or other debris and can be easily cleaned and sterilized. The tool driver of the invention also provides an improved tool driver which can maintain very close tolerances during the cutting operation which is fully operated, single handily. The invention also provides an improved tool holder for open back surgical tools, which drives a plurality of sizes of surgical tools and which has all of the above features.

While a specific embodiment of the invention has been shown and described herein for purposes of illustration, the protection afforded by any patent which may issue upon this application is not strictly limited to the disclosed embodiment; but rather extends to all structures and arrangements which fall fairly within the scope of the claims which are appended hereto:

What is claimed is:

1. A tool driver comprising a shaft having a longitudinal axis and opposite ends, a tool base secured to said shaft at one of said shaft ends, a plurality of tool engaging arms, said arms extending generally outwardly of said tool base and said shaft, said arms all defining generally the same plane, said arms being moveable generally radially outwardly of said shaft and base about pivot axes generally parallel to said longitudinal axis and generally in said plane between a tool engaging position and a retracted position, said plane being generally transverse to said longitudinal axis, an actuator on said shaft, said actuator being operatively connected to said arms and moveable on said shaft to extend and retract said arms, said shaft at the other of said shaft ends being engageable to a collet.

2. The tool driver of claim 1 further comprising a spring biasing said arms in their outward position.

3. The tool driver of claim 2 wherein said spring biases said actuator away from said tool base.

4. The tool driver of claim 1 wherein each of said arms have a distal end, said distal end having a knob surrounded by an end surface, said end surface being generally transverse to said arm, said knob extending generally radially outwardly of said tool base.

5. The tool driver of claim 1 wherein said actuator is moveable toward said tool base to retract said arms and moveable away from said tool base to extend said arms.

6. The tool driver of claim 1 wherein said tool base comprises a bottom plate extending transversely of said axis, an upstanding wall defining a cavity with said bottom plate, and a top plate enclosing said cavity.

7. The tool driver of claim 6 wherein said top and bottom plates are disc shaped.

8. The tool driver of claim 6 wherein said upstanding wall is annular.

9. The tool driver of claim 1 wherein said actuator is a tubular member slideably positioned on said shaft, said shaft having a pin secured to said shaft and extending radially outwardly thereof, said actuator having an axially extending slot in said shaft with opposite ends, said rod being within said slot, said rod being movably within said slot as said actuator moves relative to said shaft.

10. The tool driver of claim 9 wherein one of said slot ends corresponds to said arms being fully extended, the other of said slot ends corresponding to said arms being fully retracted.

11. The tool driver of claim 9 wherein said slot end most adjacent said tool base corresponds to said arms being fully retracted.

12. The tool driver of claim 9 wherein said rod has a pin secured to said rod and extending generally radially outwardly therefrom, said shaft has a slot therein, said shaft slot extending transversely of said shaft, said pin being in said shaft slot, said actuator having an elongated slot therein which extends axially and spirally around said actuator, said pin being in said actuator slot, movement of said actuator relative to said shaft moves said pin in said actuator slot and rotates said rod relative to said shaft and moves said pin in said shaft slot less than 360°.

13. The tool driver of claim 12 wherein one of said opposite ends of said longitudinally extending slot, said actuator slot, and said shaft slot corresponds to said arms in said fully extended position, and the other of said opposite ends corresponds to said arms in said fully retracted position.

14. The tool driver of claim 1 wherein said arms move generally radially outwardly of said tool base in response to generally linear movement of said actuator longitudinally of said shaft.

15. The tool driver of claim 1 wherein said movement of said actuator is generally perpendicular of said movement of said arms.

16. The tool driver of claim 1 wherein the movement of said arm is generally proportional to the movement of said actuator.

17. A tool driver comprising a shaft having a longitudinal axis on opposite ends, a tool base secured to said shaft at one of said shaft ends, a plurality of tool engaging arms, said arms extending generally outwardly of said tool base and said shaft and defining generally the same plane, said arms being movable generally radially outwardly of said shaft and base generally in said plane between a tool engaging position and a retracted position, an actuator on said shaft, said actuator being operatively connected to said arms and moveable on said shaft to extend and retract said arms, said shaft at the other of said shaft ends being engageable to a collet, said tool base having a bottom plate extending transversely of said axis, an upstanding wall defining a cavity with said bottom plate, a rod being positioned within said shaft, said rod having opposite ends, a driver being secured to said rod at one of said opposite ends, said arms being pivoted to said driver, said driver being positioned within said cavity, said wall having openings therein, said arms being positioned in said openings, said arms extending generally tangentially of said driver, said driver and said rod being rotatable about said axis to extend and retract said arms.

18. The tool driver of claim 17 wherein said driver is disc shaped.

19. The tool driver of claim 17 wherein said wall openings have opposed bearing surfaces which guide the movement of said arms to move the distal ends of said arms generally radially of said tool base and shaft.

20. The tool driver of claim 17 wherein said arms are generally rectangular in cross-section, said arms having oppositely facing guiding surfaces thereon.

21. A tool driver comprising a shaft having a longitudinal axis and opposite ends, a tool base secured to said shaft at one of said shaft ends, a plurality of tool engaging arms, said arms extending generally outwardly of said tool base and said shaft, said arms all defining generally the same plane, said arms being moveable generally radially outwardly of said shaft and base about pivot axes generally parallel to said longitudinal axis and generally in said plane between a tool engaging position and a retracted position, said plane being generally transverse to said longitudinal axis, an actuator on said shaft, said actuator being operatively connected to said arms and moveable on said shaft to extend and retract said arms, said shaft at the other of said shaft ends being engageable to a collet, a spring biasing said arms in their outward position, said actuator being moveable toward said tool base to retract said arms and moveable away from said tool base to extend said arms.

22. A tool driver comprising a shaft having a longitudinal axis and opposite ends, a tool base secured to said shaft at one of said shaft ends, a plurality of tool engaging arms, said arms extending generally outwardly of said tool base and said shaft, said arms being moveable generally radially outwardly of said shaft and base between a tool engaging position and a retracted position, an actuator on said shaft, said actuator being operatively connected to said arms and moveable on said shaft to extend and retract said arms, said shaft at the other of said shaft ends being engageable to a collet, said tool base comprises a bottom plate extending transversely of said axis, an upstanding wall defining a cavity with said bottom plate, and a top plate enclosing a cavity, said rod being positioned within said shaft, said rod having opposite ends, a driver being secured to said rod at one of said opposite ends, said arms being pivoted to said driver, said driver being positioned within said cavity, said wall having openings therein, said arms being positioned in said openings, said arms extending generally tangentially of said driver, said driver and said rod being rotatable about said axis to extend and retract said arms, said wall openings having opposed bearing surfaces which guide the movement of said arms to move the distal ends of said arms generally radially of said tool base and shaft said arms being generally rectangular in cross-section, said arms having oppositely facing guiding surfaces thereon.

23. A tool driver comprising a shaft having a longitudinal axis and opposite ends, a tool base secured to said shaft at one of said shaft ends, a plurality of tool engaging arms, said arms extending generally outwardly of said tool base and said shaft, said arms being moveable generally radially outwardly of said shaft and base between a tool engaging position and a retracted position, an actuator on said shaft, said actuator being operatively connected to said arms and moveable on said shaft to extend and retract said arms, said shaft at the other of said shaft ends being engageable to a collet, said actuator being a tubular member slideably positioned on said shaft, said shaft having a pin secured to said shaft and extending radially outwardly thereof, said actuator having an axially extending slot in said shaft with opposite ends, said rod being within said slot, said rod being movably within said slot as said actuator moves relative to said shaft, said rod being a pin secured to said rod and extending generally radially outwardly therefrom, said shaft has a slot therein, said shaft slot extending transversely of said shaft, said pin being in said shaft slot, said actuator having an elongated slot therein which extends axially and spirally around said actuator, said pin being in said actuator slot, movement of said actuator relative to said shaft moving said pin in said actuator slot and rotating said rod relative to said shaft and moving said pin in said shaft slot less than 360°, one of said opposite ends of said longitudinally extending slot and said actuator slot and said shaft slot corresponding to said arms in said fully extended position, and the other of said opposite ends corresponding to said arms in said fully retracted position.

\* \* \* \* \*